(12) United States Patent
Westlund et al.

(10) Patent No.: US 7,738,970 B2
(45) Date of Patent: ***Jun. 15, 2010

(54) MEDICAL ELECTRICAL LEAD EMPLOYING LOAD BEARING SLEEVE

(75) Inventors: Randy Westlund, Minneapolis, MN (US); Mohan Krishnan, Shoreview, MN (US); Avram Scheiner, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 668 days.

This patent is subject to a terminal disclaimer.

(21) Appl. No.: 11/643,224

(22) Filed: Dec. 21, 2006

(65) Prior Publication Data

US 2007/0123965 A1 May 31, 2007

Related U.S. Application Data

(63) Continuation of application No. 10/353,793, filed on Jan. 29, 2003, now Pat. No. 7,155,293.

(51) Int. Cl.
*A61N 1/02* (2006.01)
(52) U.S. Cl. ..................................................... 607/122
(58) Field of Classification Search .................. 607/116, 607/119, 121–123
See application file for complete search history.

(56) References Cited

U.S. PATENT DOCUMENTS

| | | |
|---|---|---|
| 4,402,328 A | 9/1983 | Doring |
| 4,573,480 A | 3/1986 | Hirschberg |
| 5,090,422 A | 2/1992 | Dahl et al. |
| 5,231,996 A | 8/1993 | Bardy et al. |

(Continued)

FOREIGN PATENT DOCUMENTS

EP 0606688 7/1994

(Continued)

OTHER PUBLICATIONS

Nakao A, Miyazaki M, Oka Y, Matsuda H, Oishi M, Kokumai Y, Kunitomo K, Isozaki H, Tanaka N. Creation and use of a composite polyurethane expanded polytetrafluoroethylene graft for hemodialysis access. Acta Med Okayama. Apr. 2000;54(2):91-94. PMID: 10806530.

(Continued)

*Primary Examiner*—Carl H Layno
*Assistant Examiner*—Brian T Gedeon
(74) *Attorney, Agent, or Firm*—Hollingsworth & Funk, LLC (57) ABSTRACT

A medical electrical lead employs a load bearing sleeve arrangement. A medical electrical lead includes an outer sleeve, having proximal and distal ends, and is formed of a first material. At least one electrical conductor is situated within the outer sleeve and extends between the proximal and distal ends of the outer sleeve. At least one electrode is electrically coupled to the electrical conductor. A load bearing sleeve extends between the proximal and distal ends of the outer sleeve. The load bearing sleeve is formed of a second material different from the first material. The load bearing sleeve offers resistance to axial loading forces applied to the lead. The load bearing sleeve can be coextensive with the outer sleeve or extend along at least the majority of the length of the outer sleeve.

25 Claims, 4 Drawing Sheets

U.S. PATENT DOCUMENTS

| | | | |
|---|---|---|---|
| 5,304,218 | A | 4/1994 | Alferness |
| 5,358,516 | A | 10/1994 | Myers et al. |
| 5,387,233 | A | 2/1995 | Alferness et al. |
| 5,466,252 | A | 11/1995 | Soukup et al. |
| 5,554,178 | A | 9/1996 | Dahl et al. |
| 5,738,220 | A | 4/1998 | Geszler |
| 5,755,762 | A | 5/1998 | Bush |
| 5,755,765 | A | 5/1998 | Hyde et al. |
| 5,782,898 | A * | 7/1998 | Dahl et al. .................. 607/119 |
| 5,871,531 | A | 2/1999 | Struble et al. |
| 5,931,862 | A | 8/1999 | Carson |
| 6,021,354 | A | 2/2000 | Warman et al. |
| 6,055,457 | A | 4/2000 | Bonner |
| 6,304,786 | B1 | 10/2001 | Heil, Jr. et al. |
| 6,584,363 | B2 | 6/2003 | Heil, Jr. et al. |
| 6,606,522 | B2 * | 8/2003 | Schell ......................... 607/122 |
| 6,704,604 | B2 * | 3/2004 | Soukup et al. .............. 607/116 |
| 6,961,621 | B2 | 11/2005 | Krishnan et al. |
| 7,155,293 | B2 * | 12/2006 | Westlund et al. ............ 607/122 |
| 2002/0147486 | A1 | 10/2002 | Soukup et al. |
| 2002/0173785 | A1 | 11/2002 | Spear et al. |

FOREIGN PATENT DOCUMENTS

| | | |
|---|---|---|
| WO | WO 00/27469 | 5/2000 |
| WO | WO0056397 | 9/2000 |
| WO | WO 01/32259 A1 | 5/2001 |
| WO | WO 01/80941 A2 | 11/2001 |

OTHER PUBLICATIONS

Bellon JM, Garcia-Carranza A, Jurado F, Garcia-Honduvilla N, Carrera-San Martin A, Bujan J, "*Peritoneal regeneration after implant of a composite prosthesis in abdominal wall*". World J Surg. Feb. 2001;25(2):147-52. PMID: 11338014.

Lumsden AB, MacDonald MJ, Kikeri D, Cotsonis GA, Harker LA, Martin LG, *Cost efficacy of duplex surveillance and prophylactic angioplasty arteriovenous ePTFE grafts*. Ann Vasc Surg. Mar. 1998;12(2):138-42. (abstract only).

Salzmann DI, Yee DC, Roach DJ, Berman SS, Williams SK. *Effects of balloon dilatation on ePTFE structural characteristics*. J Biomed Mater Res. Sep. 15, 1997;36(4):498-507. (abstract only).

Walluscheck KP, Steinhoff G, Kelm S, Haverich A. *Improved endothelial cell attachment on ePTFE vascular grafts pretreated with synthetic RGD-containing peptides*. Eur J Vasc Endovasc Surg. Oct. 1996;12(3):321-30. (abstract only).

Gillion JF, Elhadad A, Balique JG, Fourtanier G. [Two-year results of celioscopic hernioplasties using an intrperitoneal ePTFE patch. A prospective multicenter study of 184 cases. Group CHIC (Cure des hernies inguinocrurales sous coelioscopie)]. Ann Chir. 1996;50(9):799-802. French. (abstract only).

Cho JS, Ouriel K, DeWeese JA, Green RM, Chen GY, Stoughton, J. Thrombus formation on polytetrafluoroethylene surfaces: the importance of von Willebrand factor. Cardiovasc Surg. Dec. 1995;3(6):645-51. (abstract only).

Carr HM, Smyth JV, Rooney OB, Dodd PD, Sharma H, Walker MG. Limitations of in-vitro labeling of endothelial cells with indium 1 oxine. Cell Transplant. May-Jun. 1995;4(3):291-6. (abstract only).

Waldrop TC, Semba SE. Closure of oroantral communication using guided tissue regeneration and an absorbable gelatin membrane. J Periodontol. Nov. 1993;64(11):1061-6. (abstract only).

Guillemin MR, Mellonig JT, Brunsvold MA, Steffensen B. Healing in periodontal defects treated by decalcified freezedried allografts in combination with ePTFE membranes. Assessment by computerized densitometric analysis. J Clin Periodontol. Aug. 1993;20(7):520-7. (abstract only).

Geiger G, Hoevels J, Storz L, Bayer HP. Vascular grafts in below-knee femoro-popliteal bypass. A comparative study. J Cardiovasc Surg (Torino). Nov.-Dec. 1984;25(6):523-9. (abstract only).

\* cited by examiner

MEDICAL ELECTRICAL LEAD EMPLOYING LOAD BEARING SLEEVE

RELATED PATENT DOCUMENTS

This application is a continuation of U.S. patent application Ser. No. 10/353,793, now U.S. Pat. No. 7,155,293, filed on Jan. 29, 2003, to which Applicant claims priority under 35 U.S.C. §120, and which is incorporated herein by reference in its entirety.

FIELD OF THE INVENTION

The present invention relates generally to implantable leads and, more particularly, to a medical electrical lead employing a load bearing sleeve arrangement.

BACKGROUND OF THE INVENTION

Implantation of pacing and defibrillation leads in coronary vessels is becoming increasingly common as atrial and heart failure therapies become more widely accepted. Implanting and stabilizing such leads in the coronary sinus, great vein, and the branch veins is critical to the efficacy of these and other therapies. It is often desirable or necessary to remove leads implanted in cardiac structures, such as the coronary sinus vasculature, for various reasons. Removal of these leads is problematic, especially if coil electrodes are employed on the lead.

Presently, there are no widely accepted extraction tools available for the safe removal of coronary vein leads. Various tools have been developed for removing right ventricular leads and right atrial leads, for example, such as mechanical dissection sheaths, electrocautery sheaths, laser sheaths, and other powered sheaths. Such tools, however, are not suited for use within thin walled vessels. Presently available extraction tools, for example, can only be safely used to enter the proximal portions of the coronary sinus. The risk of significant damage to the vasculature is very high, which can result in cardiac tamponade and death. Consequently, physicians are presently limited to using locking stylets and simple traction as a means of removing coronary vein leads. Use of traction to remove right and left side leads is known to impart significant axial forces on the leads. Excessively high levels of axial loading imparted to conventional leads during lead extraction can result in lead damage or destruction.

Various types of coatings applied to the electrodes have also been considered in order to facilitate easier removal of coronary vein leads. Although the extractability characteristics of leads can be improved using certain lead coatings, use of such coatings has been found to significantly reduce lead stability. For example, coated lead dislodgment rates of 25%-50% have been observed. As such, the gains in lead extractability realizable through use of conventional lead coatings are achieved at the cost of reduced lead stability.

There is a need in the industry for an improved coronary vein lead that exhibits improved extractability characteristics. There exists a further need for such a lead that can withstand relatively high axial loads associated with right and left side lead extraction. The present invention fulfills these and other needs, and provides a number of advantages over prior art approaches.

SUMMARY OF THE INVENTION

The present invention is directed to a medical electrical lead employing a load bearing sleeve arrangement. According to one embodiment, a medical electrical lead includes an outer sleeve, having proximal and distal ends, and is formed of a first material. At least one electrical conductor is situated within the outer sleeve and extends between the proximal and distal ends of the outer sleeve. At least one electrode is electrically coupled to the electrical conductor. A load bearing sleeve extends between the proximal and distal ends of the outer sleeve. The load bearing sleeve is formed of a second material different from the first material. The load bearing sleeve offers resistance to axial loading forces applied to the lead.

The first material of the outer sleeve is preferably formed from a flexible polymer material, and the second material of the load bearing sleeve is formed from an ultra-high molecular weight polymeric material. By way of example, the first material of the outer sleeve can be silicone or polyurethane, and the second material of the load bearing sleeve can be PTFE or ePTFE.

The load bearing sleeve extends along at least a majority of the length of the outer sleeve. The load bearing sleeve can, for example, be substantially coextensive with the outer sleeve. The load bearing sleeve can be entirely encompassed by the outer insulating sleeve. Alternatively, portions of the load bearing sleeve proximate an electrode or other transition can emerge from the interior of the lead body so as to cover the electrode or transition. The load bearing sleeve submerges into the lead body distal of the electrode/transition in configurations in which the lead body extends beyond the subject electrode/transition.

The electrical conductor can be configured as a coil conductor, and the load bearing sleeve can be situated within a longitudinally extending cavity of the coil conductor. The longitudinally extending cavity of the load bearing sleeve in such a configuration defines an open lumen of the lead. The open lumen can be dimensioned to receive a guide wire, a sensor, a stylet or other implement or instrument.

In accordance with another embodiment, a medical electrical lead of the present invention includes an outer sleeve formed of a first material and an electrical conductor situated within the outer sleeve which extends between the proximal and distal ends of the outer sleeve. At least one electrode is electrically coupled to the electrical conductor. A load bearing sleeve extends between the proximal and distal ends of the outer sleeve. A majority of the length of the load bearing sleeve is positioned within the outer sleeve. The load bearing sleeve is formed of a second material having a tensile strength greater than that of the first material of the outer sleeve and a tensile elongation less than that of the first material. An inner surface of a portion of the load bearing sleeve extends over an outer surface of the at least one electrode, and an outer surface of the load bearing sleeve portion is exposed through a gap in the outer sleeve.

According to another embodiment, a method of implanting a medical electrical lead into a cardiac structure of a patient's heart involves providing a guiding catheter for longitudinally guiding the lead. The lead preferably has a construction which incorporates a load bearing sleeve arrangement. The implantation method involves inserting the guiding catheter into a chamber of the patient's heart via an access vessel. The lead is inserted through the guiding catheter via the open lumen to implant the lead within or on the cardiac structure.

In one approach, the implantation method involves providing a guide wire for longitudinally guiding the lead. The guide wire is inserted through the guiding catheter into the cardiac structure. The lead is inserted through the guiding catheter and over the guide wire via the open lumen to implant the lead within or on the cardiac structure. According to another approach, a sensor catheter can be inserted through the open lumen to assist in locating the cardiac structure.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

While the invention is amenable to various modifications and alternative forms, specifics thereof have been shown by way of example in the drawings and will be described in detail hereinbelow. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

In broad and general terms, the present invention is directed to a medical electrical lead which employs a load bearing sleeve arrangement. More particularly, embodiments of the present invention are directed to a medical electrical lead having an outer insulating sleeve and an inner load bearing sleeve. In certain embodiments, the load bearing sleeve extends along a majority of the outer sleeve length. For example, the load bearing sleeve can be substantially coextensive with the outer sleeve of the medical electrical lead. In other embodiments, the load bearing sleeve can be discontinuous or perforated in certain locations, such as at an electrode location.

The medical electrical lead can be configured such that one or more electrodes of the lead are positioned proximate an outer surface of the load bearing sleeve. The lead can also be configured such that one or more electrodes of the lead are positioned proximate an inner surface of the load bearing sleeve. In one configuration, for example, the load bearing sleeve is positioned between the outer sleeve and a coil conductor of the medical electrical lead.

The load bearing sleeve can be disposed within a medical electrical lead so as to define an open inner lumen of the lead. The open lumen can be used to receive a guide wire for over-the-wire implant procedures. The open lumen can also be dimensioned to receive a sensor catheter. According to one configuration, two load bearing sleeves can be used: one that defines an inner lumen of the lead, and a second that is situated between a lead conductor(s) and the outer insulating sleeve of the lead. Other configurations are possible, including use of one or more load bearing sleeves to define one or more lumens of a medical electrical lead.

The load bearing sleeve is preferably formed from a material having a tensile strength greater than that of the outer insulating sleeve. For example, the load bearing sleeve can have a tensile strength greater than about 5,500 psi, and the outer insulating sleeve can have a tensile strength of less than about 5,000 psi. The tensile elongation of the load bearing sleeve is preferably significantly less than that of the outer insulating sleeve. For example, the load bearing sleeve can have a tensile elongation of less than 100%, and the outer insulating sleeve can have a tensile elongation of 300%-1000% or more.

The load bearing sleeve is preferably formed from an ultra-high molecular weight polymeric material, such as PTFE (polytetrafluoroethylene) or ePTFE (expanded polytetrafluoroethylene), for example. The outer insulating sleeve can be formed from materials commonly used for a medical electrical lead, such as silicone or polyurethane.

A medical electrical lead of the present invention is particularly well suited for use with left side pacing and cardioversion/defibrillation devices, it being understood that advantages of the present invention can be realized in right side lead systems. As was discussed briefly above, pacing and defibrillation leads implanted in the coronary vessels are becoming more common as left atrial and left ventricular therapies become more accepted. In the absence of standard extraction tools, relatively high axial loads must typically be applied to such leads during lead extraction. The integrity of such a lead fabricated using conventional techniques can be compromised if the lead is subjected to excessively high axial forces.

A medical electrical lead fabricated in accordance with the present invention advantageously provides for improved axial loading characteristics over conventional leads. Left side leads, for example, can be fabricated to incorporate a load bearing sleeve in a manner described herein to significantly enhance the extractability performance of such leads.

An important advantage realized by employing a load bearing sleeve in a medical electrical lead of the present invention concerns a significant improvement in axial loading characteristics as compared to many conventional designs. It is appreciated in the art that right sided leads generally require nigh axial loads for extraction. Left sided leads require substantially lower axial loads for extraction, but are smaller and more flexible than right sided leads, typically resulting in generally less robust designs. In accordance with the principles of the present invention, improved axial loading characteristics are achieved for right sided leads, while inclusion of a load bearing sleeve in left sided leads provides additional robustness to such implementations.

Figure 1:
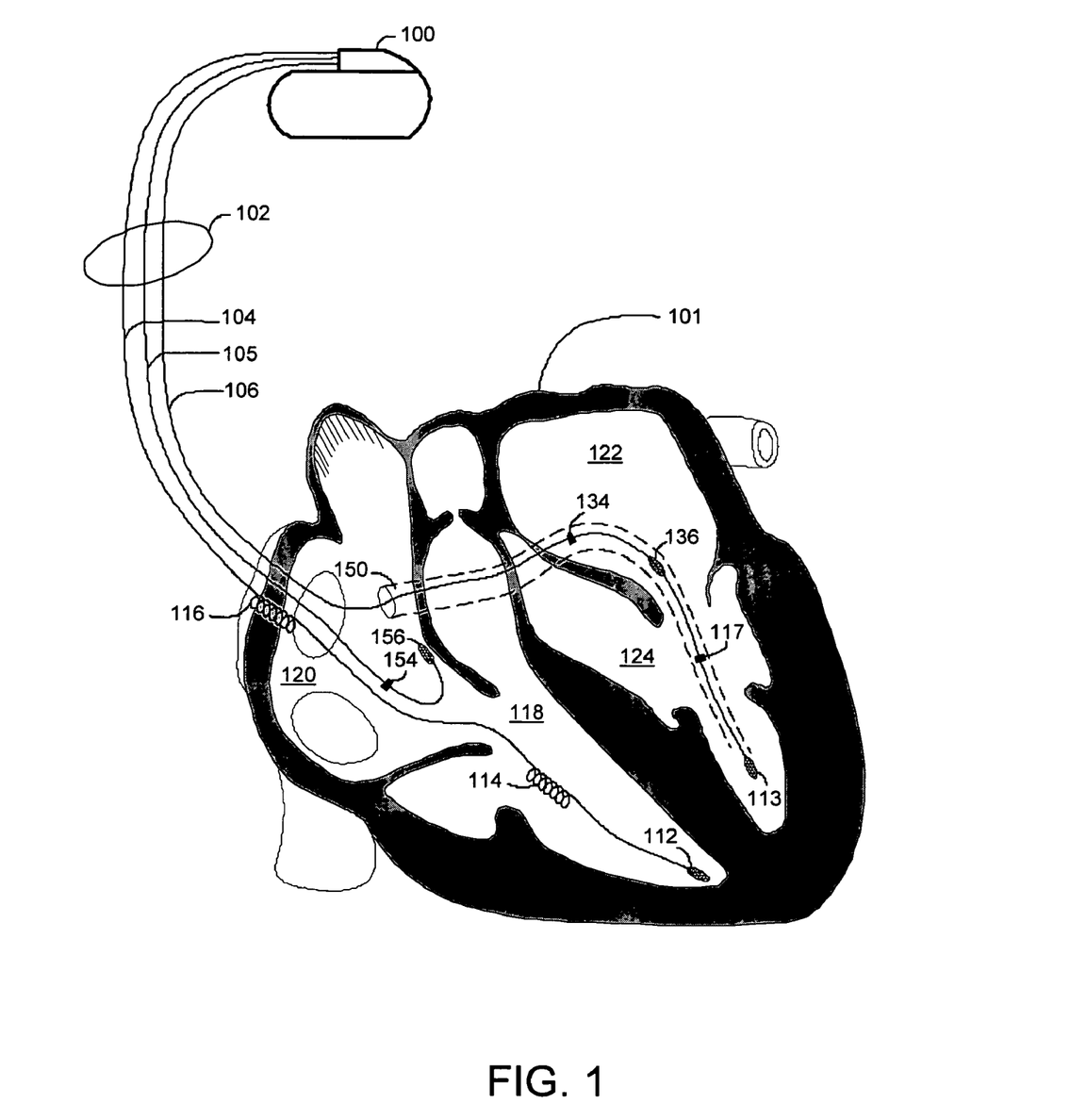
FIG. 1 is a partial sectional view of a human heart and a lead system employing left and right side leads comprising pacing and cardioversion/defibrillation electrodes.

Referring to FIG. 1 of the drawings, there is shown one embodiment of an implantable medical device which includes a cardiac function management (CFM) device 100 electrically and physically coupled to an intracardiac lead system 102. The intracardiac lead system 102 is implanted in a human body with portions of the intracardiac lead system 102 inserted into a heart 101. The intracardiac lead system 102 is used to detect and analyze electric cardiac signals produced by the heart 101 and to provide electrical energy to the heart 101 under certain predetermined conditions to treat cardiac arrhythmias.

The intracardiac lead system 102 includes one or more electrodes used for pacing, sensing, or defibrillation. In the particular embodiment shown in FIG. 1, the intracardiac lead system 102 includes a right ventricular lead system 104, a right atrial lead system 105, and a left atrial/ventricular lead system 106. In one embodiment, the right ventricular lead system 104 is configured as an integrated bipolar pace/shock lead. One, some, or all of the lead systems shown in FIG. 1 can be configured to include a load bearing sleeve arrangement of the present invention.

It is understood that the implantable medical device shown in FIG. 1 can employ a single lead for use in a single heart chamber or multiple heart chambers. It is also understood that a medical electrical lead of the present invention can incorporate one or more electrodes, including one or more of a pacing electrode, cardioversion/defibrillation electrode, and monitoring electrode, for example.

The right ventricular lead system 104 includes an SVC-coil 116, an RV-coil 114, and an RV-tip electrode 112. The RV-coil 114, which may alternatively be configured as an RV-ring electrode, is spaced apart from the RV-tip electrode 112, which is a pacing electrode for the right ventricle.

The right atrial lead system 105 includes an RA-tip electrode 156 and an RA-ring electrode 154. The RA-tip 156 and RA-ring 154 electrodes may provide respectively pacing pulses to the right atrium of the heart and detect cardiac signals from the right atrium. In one configuration, the right atrial lead system 105 is configured as a J-lead.

In this configuration, the intracardiac lead system 102 is shown positioned within the heart 101, with the right ventricular lead system 104 extending through the right atrium 120 and into the right ventricle 118. In particular, the RV-tip electrode 112 and RV-coil electrode 114 are positioned at appropriate locations within the right ventricle 118. The SVC-coil 116 is positioned at an appropriate location within the right atrium chamber 120 of the heart 101 or a major vein leading to the right atrium chamber 120 of the heart 101. The RV-coil 114 and SVC-coil 116 depicted in FIG. 1 are defibrillation electrodes.

An LV-tip electrode 113 and an LV-ring electrode 117 are inserted through the coronary venous system and positioned adjacent to the left ventricle 124 of the heart 101. The LV-ring electrode 117 is spaced apart from the LV-tip electrode 113, which is a pacing electrode for the left ventricle. Both the LV-tip 113 and LV-ring 117 electrodes may also be used for sensing the left ventricle providing two sensing sites within the left ventricle. The left atrial/left ventricular lead system 106 further includes an LA-tip 136 and LA-ring 134 electrode positioned adjacent to the left atrium 122 for pacing and sensing the left atrium 122 of the heart 101.

The left atrial/left ventricular lead system 106 includes endocardial pacing leads that are advanced through the superior vena cava (SVC), the right atrium 120, the valve of the coronary sinus, and the coronary sinus 150 to locate the LA-tip 136, LA-ring 134, LV-tip 113 and LV-ring 117 electrodes at appropriate locations adjacent to the left atrium and ventricle 122, 124, respectively. In one example, left atrial/ventricular lead placement involves creating an opening in a percutaneous access vessel, such as the left subclavian or left cephalic vein. The left atrial/left ventricular lead 106 is guided into the right atrium 120 of the heart via the superior vena cava.

From the right atrium 120, the left atrial/left ventricular lead system 106 is deployed into the coronary sinus ostium, the opening of the coronary sinus 150. The lead system 106 is guided through the coronary sinus 150 to a coronary vein of the left ventricle 124. This vein is used as an access pathway for leads to reach the surfaces of the left atrium 122 and the left ventricle 124 which are not directly accessible from the right side of the heart. Lead placement for the left atrial/left ventricular lead system 106 may be achieved via the subclavian vein access and a preformed guiding catheter for insertion of the LV and LA electrodes 113, 117, 136, 134 adjacent the left ventricle 124 and left atrium 122, respectively. In one configuration, the left atrial/left ventricular lead system 106 is implemented as a single-pass lead.

The lead system further includes a terminal end for establishing physical and electrical connection with a connector block of the CFM device 100. The CFM device can be configured as, or incorporate functions of, a pacemaker, cardioverter, defibrillator, cardiac monitor, re-synchronizer or a device that incorporates the functions of two or more of these devices.

Figure 2:
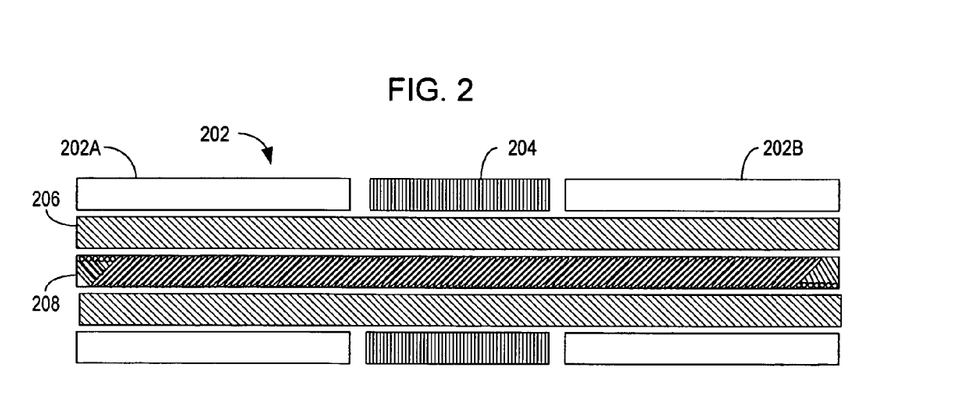
FIG. 2 is a sectional view of a medical electrical lead employing a load bearing sleeve arrangement in accordance with an embodiment of the present invention.

Turning now to FIG. 2, there is illustrated a sectional view of a medical electrical lead which incorporates a load bearing sleeve arrangement in accordance with an embodiment of the present invention. The sectional view of FIG. 2 is taken at a region of the lead which encompasses an electrode. The electrode is generally representative of a defibrillation electrode or a pacing electrode, such as a platinum/iridium electrode, and the electrical conductor that electrically connects with the electrode is generally representative of a coil conductor, such as a single or multiple filar coil conductor, or a cable. It is understood that other electrode and conductor configurations can be employed in a medical electrical lead of the present invention, and that the particular configurations shown and described herein are intended to be non-limiting illustrative examples.

According to the embodiment illustrated in FIG. 2, the medical electrical lead includes an outer insulating sleeve 202, which can be formed from a conventional material suitable for implantable leads. By way of example, the insulating sleeve 202 can be fabricated from silicone, polyurethane, or other biocompatible, flexible material. An electrode 204 is shown positioned in a gap formed between adjacent sections 202A, 202B of the outer sleeve 202. The interfaces between the electrode 204 and respective outer sleeve sections 202A, 202B can be sealed using conventional techniques.

In FIG. 2, the electrode 204 is representative of a cardioversion/defibrillation electrode. Appropriate electrical connections are made between the electrode 204 and the electrical conductor 208 of the lead. By way of example, electrical connections that breach the load bearing sleeve, such as some crimping and swaging operations, in isolated areas may be used.

In the illustrative embodiment of FIG. 2, a load bearing sleeve 206 is shown disposed within the lead, such that all of the load bearing sleeve 206 is surrounded by the outer insulating sleeve 202. In other embodiments, some of which are described below, most of the load bearing sleeve 206 is surrounded by the outer insulating sleeve 202, but one or more sections of the load bearing sleeve 206 can emerge from the interior of the lead body at particular locations, such as at electrode or transition locations.

The lead, according to this configuration, includes a central lumen within which a coil conductor 208 is situated.

Although a single lumen is shown for simplicity, it is understood that a medical electrical lead of the present invention can include two, three, or more lumens. Moreover, it is understood that a lead of the preset invention can include one or more open lumens, closed lumens, or a combination of open and closed lumens. Such lumens can be dimensioned to receive steering tendons, a guide wire, finishing wire, sensor, instrument, or other type of catheter, for example. A lumen can also be dimensioned to receive a stylet, although the load bearing sleeve arrangement of the present invention can obviate the need for a conventional stylet in many applications. A lumen of such a lead can be provided with a lubricious sleeve or coating, such as a PTFE or ePTFE sleeve, for example.

In the configuration shown in FIG. 2, the load bearing sleeve 206 is disposed entirely within the lead (i.e., encompassed by the outer sleeve 202) and extends along the length of the lead or some majority portion of the lead. As shown, the load bearing sleeve 206 is positioned within the lead lumen, it being understood that the specific location of the load bearing sleeve 206 within the lead structure can be varied.

In this configuration, the coil conductor 208 is positioned within the load bearing sleeve 206. The hollow coil conductor may thus define an inner lumen of the lead, which can be an open or closed lumen. In a configuration in which a solid (i.e., non-hollow) conductor is employed, such as a cable, no such inner lumen would be defined within the load bearing sleeve 206 depicted in FIG. 2. However, it can be appreciated that the load bearing sleeve 206 can be dimensioned to receive a solid electrical conductor along with one or more other elements, such as a sensor catheter for example. Such a sensor catheter can incorporate a pressure sensor, an oxygen sensor or a temperature sensor, for example.

In the case of an over-the-wire lead configuration, by way of example, the load bearing sleeve 206 is dimensioned to receive a hollow coil conductor 208. The coil conductor 208 is dimensioned to receive a guide wire suitable for left heart chamber over-the-wire lead implant procedures, for example. The coil conductor 208 is preferably provided with a lubricious sleeve, liner, or coating. In one configuration, the coil conductor 208 can be provided with a lubricous load bearing sleeve, in addition to, or exclusive of, the load bearing sleeve 206. An example of one such variation in configuration will be described below with reference to FIG. 6.

The lubricious material provided within the coil conductor 208 preferably has a low-energy surface that inhibits platelet adhesion. A suitable lubricious material that provides a low-energy surface for this usage is ePTFE. Such a surface advantageously provides for enhanced tactile feedback to the physician during use of the over-the-wire lead arrangement.

As was discussed previously, the load bearing sleeve 206 is preferably formed from a material having a tensile strength greater than that of the outer insulating sleeve 202. According to one configuration, the load bearing sleeve 206 has a tensile strength greater than about 5,500 psi, and the outer insulating sleeve 202 has a tensile strength of less than about 5,000 psi. The tensile elongation of the load bearing sleeve 206 is preferably less than 100%, and that of the outer insulating sleeve is preferably 300%-1000% or more. In general, the load bearing sleeve 206 can have a wall thickness ranging between about 0.001 inches and about 0.01 inches. According to one particular configuration, the load bearing sleeve 206 has a wall thickness ranging between about 0.002 inches and about 0.006 inches.

The load bearing sleeve 206 is preferably formed from an ultra-high molecular weight polymeric material, such as PTFE or ePTFE, for example. It has been determined that leads with substantial amounts of exposed ePTFE have demonstrated high rates of dislodgment. Extensive use of ePTFE within the interior of a medical electrical lead, rather than on the exterior, provides for a more robust lead implementation, which can withstand higher levels of axial loading without adversely affecting performance as compared to conventional leads.

The electrical characteristics of a medical electrical lead of the present invention can be selectively altered by judicious selection of the electrode/load bearing sleeve configuration. By way of example, variations in electrode surface exposure and coverage can be achieved by implementing designs in which the electrode is fully exposed (i.e., not covered by the load bearing sleeve), entirely covered by the load bearing sleeve, or partially covered by the load bearing sleeve.

Varying the level of electrode exposure/coverage can result in varying several electrical characteristics of the lead electrodes, such as the polarization characteristics of the lead electrodes. Moreover, different current distributions can be achieved by selectively altering the level of electrode exposure/coverage. In some configurations, an increase in impedance may result, but enhancements in other mechanical or electrical characteristics, such as electrode polarization and/or current distribution, can offset such increases in impedance.

Figure 3:
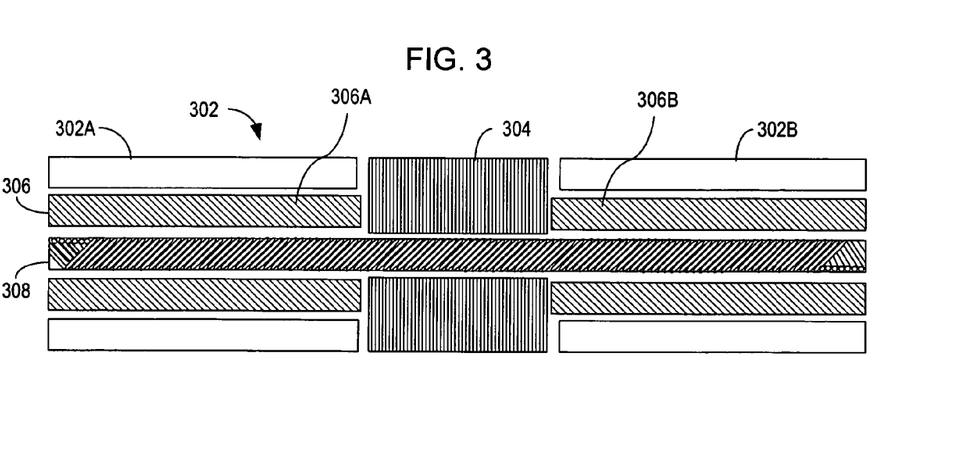
FIG. 3 is a sectional view of a medical electrical lead employing a load bearing sleeve arrangement in accordance with another embodiment of the present invention.

FIG. 3 illustrates another embodiment of a medical electrical lead which employs a load bearing sleeve arrangement 306 in accordance with the principles of the present invention. According to this embodiment, the lead includes an outer insulating sleeve 302 and an electrode 304 situated within a gap formed between adjacent sections 302A, 302B of the outer sleeve 302. In this particular configuration, a load bearing sleeve 306 is discontinuous at the region proximate the electrode 304. For example, the load bearing sleeve 306 can be formed to have a discontinuity at each of the electrodes 304 that are situated along the length of the lead.

As shown, electrode 304 is situated within a gap formed between adjacent sections 306A, 306B of the load bearing sleeve 306. The electrode 304 is connected to the electrical conductor 308, which can be a coil conductor for example, and protrudes through the load bearing sleeve 306 and the outer insulating sleeve 302. In a typical configuration, the electrode 304 is generally flush with respect to the outer surface of the outer insulating sleeve 302. A suitable sealing material or arrangement is employed between the electrode 304 and the adjacent outer sleeve sections 302A, 302B and load bearing sleeve sections 306A, 306B, respectively.

Figure 4:
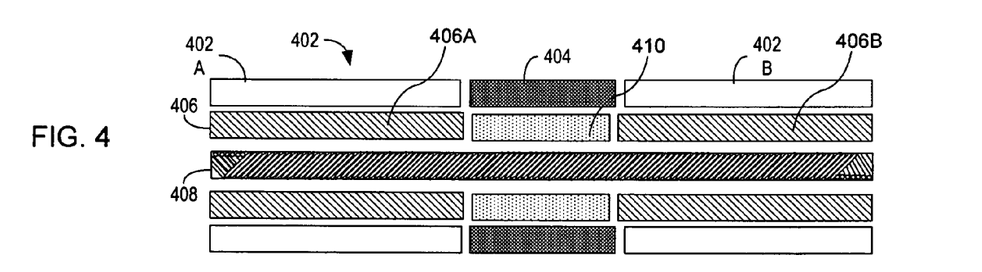
FIG. 4 is a sectional view of a medical electrical lead employing a load bearing sleeve arrangement in accordance with a further embodiment of the present invention.

The embodiment of a medical electrical lead shown in FIG. 4 is similar to that shown in FIG. 3, in that the load bearing sleeve arrangement 406 includes a discontinuity at a location proximate the electrode 404. In this embodiment, an electrically conductive element, material, or filler 410 is employed at an interface between the electrode 404 and the electrical conductor 408. The filler or element 410 provides for conduction of electrical current between the electrode 404 and conductor 408, and can be sized to provide a desired outer surface profile of the lead. The element 410 can, if desired, be implemented to intimately connect with adjacent edges of adjacent load bearing sleeve sections 406A, 406B, such as through use of known mechanical or chemical/adhesion means.

Figure 5A:
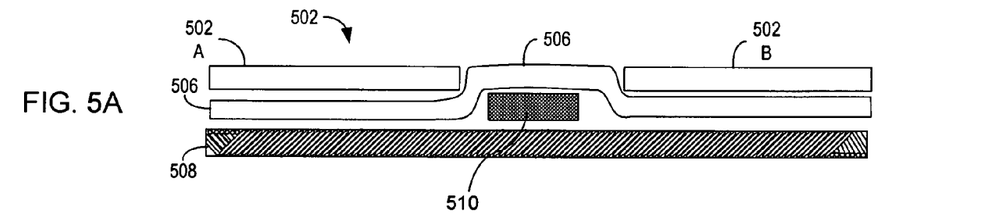
FIGS. 5A and 5B are partial sectional views of a medical electrical lead employing a load bearing sleeve arrangement in accordance with yet another embodiment of the present invention.
Figure 5B:
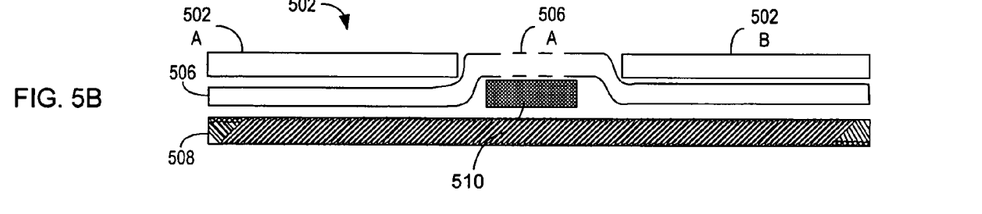

FIGS. 5A and 5B illustrate variations of another embodiment of the present invention. According to this embodiment, a load bearing sleeve 506 is positioned within the lead such that most of the load bearing sleeve 506 is encompassed by an outer insulating sleeve 502. In a region proximate an electrode 510, however, the load bearing sleeve 506 emerges from the interior of the lead body so as to extend over the electrode

510. The load bearing sleeve 506 returns to the sub-surface of the lead body after passing the distal end of the electrode 510. In a configuration in which the lead body does not extend beyond the electrode, as in the case of a tip electrode for example, the load bearing sleeve need not return to the lead body sub-surface.

In the embodiment of FIGS. 5A and 5B, the load bearing sleeve 506 is not severed at the region proximate the electrode 510, but remains continuous along its length. In the variation shown in FIG. 5B, the exposed portion of the load bearing sleeve 506A covering the electrode 510 can include perforations.

It is noted that the bent or bulged section of the load bearing sleeve 506 proximate the electrode 510 can be pre-formed or formed at the time of lead fabrication. It is further noted that the wall thickness of the bent or bulged section of the load bearing sleeve 506 proximate the electrode 510 can be different from that of other sections of the load bearing sleeve 506. For example, the thickness of the load bearing sleeve wall in the bent or bulged region can be less than that of the non-bent portions of the load bearing sleeve 506, such as by up to about 50% less in thickness.

The embodiment shown in FIGS. 5A and 5B provides the desired improvement in axial loading characteristics while not adversely contributing to implant instability and lead dislodgment. It is known that ePTFE, for example, is a material that prevents or inhibits tissue in-growth (e.g., fibrotic encapsulation or any other form of cellular adhesion). As was discussed above, extensive use of ePTFE as an outer sleeve of an implantable medical electrical lead has been associated with high lead dislodgment rates. However, limiting the external use of ePTFE primarily at the electrode regions of a medical electrical lead in accordance with the principles of the present invention avoids such lead dislodgment problems and provides for significantly improved axial loading characteristics.

Figure 6:
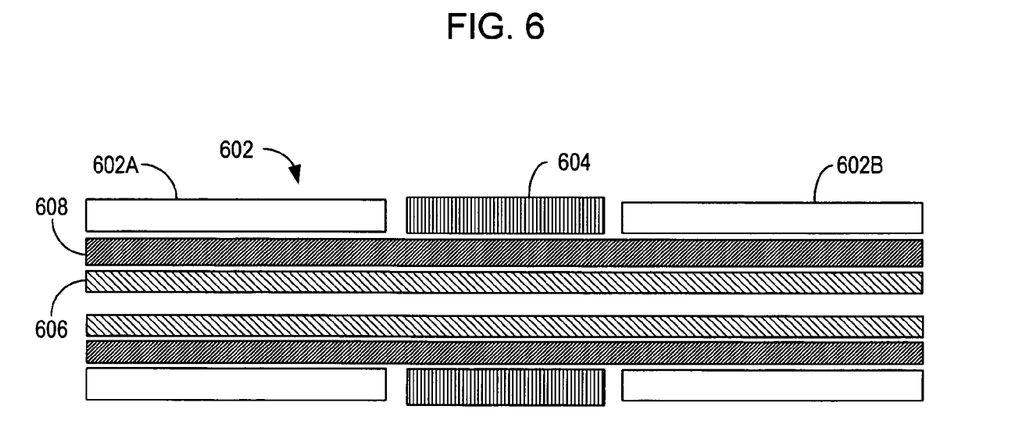
FIG. 6 is a sectional view of a medical electrical lead employing a load bearing sleeve arrangement in accordance with a further embodiment of the present invention.

A further embodiment of a medical electrical lead implemented in accordance with the present invention is depicted in FIG. 6. According to this embodiment, the load bearing sleeve 606 is disposed within a lumen defined within the interior of a coil electrode 608. The coil electrode 608, in this configuration, is situated between the inner surface of the outer insulating sleeve 602 and the outer surface of the load bearing sleeve 606. The electrode 604 is shown positioned in a gap formed between adjacent sections 602A, 602B of the outer sleeve 602, and electrically connects with the coil electrode 608.

In this configuration, the load bearing sleeve 606 defines an inner lumen of the medical electrical lead. This configuration is particularly well-suited for use in over-the-wire implantation procedures, as the interior surface of the load bearing sleeve 606 preferably defines a lubricious surface. In an alternative configuration, a second load bearing sleeve can be situated between the coil conductor 608 and the outer insulating sleeve 602 in a manner previously discussed.

A medical electrical lead incorporating a load bearing sleeve in accordance with the principles of the present invention can be used in a variety of medical procedures. By way of example, a method of implanting a medical electrical lead into a cardiac structure of a patient's heart involves use of a guiding catheter for longitudinally guiding the lead. The lead has an open lumen and includes an outer sleeve formed of a first material. A coil conductor is situated within the outer sleeve and extends between proximal and distal ends of the outer sleeve. At least one electrode is electrically coupled to the coil conductor. The lead further includes a load bearing sleeve that extends between the proximal and distal ends of the outer sleeve. The load bearing sleeve is formed of a second material different from the first material. The load bearing sleeve offers resistance to axial loading forces applied to the lead.

The procedure involves inserting the guiding catheter into a chamber of the patient's heart via an access vessel. The procedure further involves inserting the lead through the guiding catheter via the open lumen to implant the lead within or on the cardiac structure.

According to one procedure, a guide wire is provided for longitudinally guiding the lead. The procedure involves inserting the guide wire through the guiding catheter into the cardiac structure. The lead is inserted through the guiding catheter and over the guide wire via the open lumen to implant the lead within or on the cardiac structure.

In another procedure, a sensor catheter is provided. The procedure involves inserting the sensor catheter through the open lumen to assist in locating the cardiac structure. The cardiac structure can be a cardiac vessel, such as a left side coronary vessel, for example. These and other procedures can be performed using a medical electrical lead having improved axial load characteristics in accordance with the principles of the present invention.

A medical electrical lead of the present invention may also be configured to include a lead stabilization mechanism in combination with a load bearing sleeve arrangement. A lead stabilization mechanism, according to one embodiment, employs an adhesion site or sites at strategic locations on the lead, including electrically active and/or electrically inactive locations of the lead. A polymer outer sleeve or coating of the lead provides for improved lead extractability, while the adhesion sites provide for increased stability at selected locations of the lead.

The lead, according to this embodiment, has a sleeve arrangement which includes one or more adhesion sites provided at one or more of the first lead locations. The adhesion sites promote tissue in-growth or attachment between the adhesion sites and cardiac tissue contacting the adhesion sites to enhance stabilization of the implantable lead. The cardiac tissue may represent tissue of a cardiac structure of the heart or coronary vasculature of the heart.

The adhesion sites, in one embodiment, define apertures in the sleeve at one or more first locations of the sleeve. For example, the adhesion sites may comprise exposed portions of one or more of the electrodes or other exposed portions of the lead's insulation or covering. According to another embodiment, the adhesion sites include a structure having a porous surface that promotes cardiac tissue in-growth or attachment at the adhesion sites. For example, a metallic annular structure may be disposed at the adhesion site. A metallic ring, for example, having porous surface characteristics may be employed to promote cellular adhesion at the adhesion site. The annular structure may incorporate an electrode, sensor or drug delivery arrangement. An annular electrode structure, for example, may incorporate a sensing, pacing or shocking electrode.

In accordance with a further embodiment, the adhesion sites comprise a material that promotes cardiac tissue in-growth or attachment at the adhesion sites. For example, the first material may comprise a first polymer material that substantially prevents tissue in-growth between the first locations and cardiac tissue contacting the first locations. The adhesion sites, in contrast, comprise a second polymer material that promotes tissue in-growth or attachment between the adhesion sites and cardiac tissue contacting the adhesion sites. The second polymer material may, for example, have a porosity, pore sizes or distribution of pore sizes that differ from that of the first polymer material. By way of further example, the second polymer material may differ in terms of hydrophobicity relative to the first polymer material.

In one embodiment, the first material comprises a first type of PTFE, and a second material of the adhesion sites comprises a second type of PTFE. In one particular arrangement, the first type of PTFE comprises a first type of ePTFE, and the second type of PTFE comprises a second type of ePTFE. The second type of ePTFE preferably differs from the first type of ePTFE in terms of one or more of porosity, pore sizes or distribution of pore sizes.

A suitable lead stabilization system and method that can be used in combination with a load bearing sleeve arrangement as described herein is disclosed in commonly owned U.S. Pat. No. 6,961,621, which is hereby incorporated herein by reference.

It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A medical electrical lead, comprising:
   an outer sleeve formed of a first polymer material, the outer sleeve having a proximal end and a distal end;
   an electrical conductor situated relative the outer sleeve and extending between the proximal and distal ends of the outer sleeve, the electrical conductor comprising a coil conductor;
   at least one electrode electrically coupled to the electrical conductor;
   a first load bearing sleeve extending between the proximal and distal ends of the outer sleeve and situated within a longitudinally extending cavity of the coil conductor, the first load bearing sleeve formed of a second polymer material different from the first polymer material; and
   a second load bearing sleeve formed of a third polymer material different from the first material and situated between the outer sleeve and the coil conductor, the first and second load bearing sleeves offering resistance to axial loading forces applied to the lead, each of the second polymer material and the third polymer material having tensile strength greater than that of the first polymer material, and the first polymer material having tensile elongation greater than that of each of the second polymer material and the third polymer material.

2. The lead of claim 1, wherein one or both of the first and second load bearing sleeves extends along at least a majority of a length of the outer sleeve.

3. The lead of claim 1, wherein one or both of the first and second load bearing sleeves is substantially coextensive with the outer sleeve.

4. The lead of claim 1, wherein an outer surface of the electrode is situated at an exposed portion of the outer sleeve, and an inner surface of the electrode contacts an electrode interface surface of the second load bearing sleeve, such that the electrode is electrically coupled to the electrical conductor through the electrode interface surface.

5. The lead of claim 1, wherein an outer surface of the electrode is situated at an exposed portion of the outer sleeve, and an inner surface of the electrode is electrically coupled to the electrical conductor via a gap in a surface of the second load bearing sleeve.

6. The lead of claim 5, further comprising an electrically conductive filler or element provided within the gap.

7. The lead of claim 1, wherein the electrode is situated within a gap in the outer sleeve and a portion of the second load bearing sleeve protrudes through the gap so as to extend over an outer surface of the electrode, such that an inner surface of the electrode is electrically coupled to the electrical conductor.

8. The lead of claim 7, wherein the third polymer material of the second load bearing sleeve comprises a biocompatible material.

9. The lead of claim 1, wherein a longitudinally extending cavity of the first load bearing sleeve defines an open lumen of the lead.

10. The lead of claim 9, wherein the open lumen is dimensioned for receiving a guide wire or a sensor catheter.

11. The lead of claim 1, wherein the first polymer material of the outer sleeve comprises silicone or polyurethane, and one or both of the second polymer material and third polymer material of the respective first and second load bearing sleeves comprises PTFE or ePTFE.

12. The lead of claim 1, wherein the first polymer material of the outer sleeve has a tensile strength of less about 5,000 psi, and one or both of the second polymer material and third material of the respective first and second load bearing sleeves has a tensile strength greater than about 5,500 psi.

13. The lead of claim 1, wherein the first polymer material of the outer sleeve has a tensile elongation of greater than about 300%, and one or both of the second polymer material and third polymer material of the respective first and second load bearing sleeves has a tensile elongation of less than about 100%.

14. The lead of claim 1, wherein one or both of the first and second load bearing sleeves has a wall thickness ranging between about 0.001 inches and about 0.01 inches.

15. The lead of claim 1, wherein one or both of the first and second load bearing sleeves has a wall thickness ranging between about 0.002 inches and about 0.006 inches.

16. A medical electrical lead, comprising:
   an outer sleeve formed of a first material, the outer sleeve having a proximal end and a distal end, the outer sleeve comprising:
      one or more first locations comprising a third material that substantially prevents tissue in-growth between the first locations and cardiac tissue contacting the first locations; and
      one or more adhesion sites provided at the one or more first locations, the adhesion sites promoting tissue in-growth or attachment between the adhesion sites and cardiac tissue contacting the adhesion sites;
   an electrical conductor situated within the outer sleeve and extending between the proximal and distal ends of the outer sleeve;
   at least one electrode electrically coupled to the electrical conductor, at least one of the adhesion sites comprising an exposed portion of the at least one electrode; and
   a load bearing sleeve extending between the proximal and distal ends of the outer sleeve, the load bearing sleeve formed of a second material differing from the first material, the load bearing sleeve offering resistance to axial loading forces applied to the lead.

17. The lead of claim 16, wherein one or more of the adhesion sites comprises an aperture in the outer sleeve at the one or more first locations of the outer sleeve.

18. The lead of claim 16, wherein one or more of the adhesion sites comprises a material that promotes cardiac tissue in-growth or attachment.

19. The lead of claim 16, wherein one or more of the adhesion sites comprises a structure having a porous surface that promotes cardiac tissue in-growth or attachment.

20. The lead of claim 16, wherein the third material comprises a first polymer material that substantially prevents tissue in-growth between the first locations and cardiac tissue contacting the first locations, and one or more of the adhesion sites comprises a fourth polymer material that promotes tissue in-growth or attachment with cardiac tissue.

21. The lead of claim 20, wherein the fourth polymer material has a porosity differing from that of the third polymer material.

22. The lead of claim 20, wherein the fourth polymer material has an average pore size differing from that of the third polymer material.

23. The lead of claim 20, wherein the fourth polymer material has a distribution of pore sizes differing from that of the third polymer material.

24. The lead of claim 20, wherein the fourth polymer material has a hydrophobicity differing from that of the third polymer material.

25. The lead of claim 16, wherein the second and third materials comprise ePTFE.

* * * * *